US009545452B2

United States Patent
Wang et al.

(10) Patent No.: US 9,545,452 B2
(45) Date of Patent: Jan. 17, 2017

(54) BIOMINERAL AND METAL BINDING LIPOSOMES, THEIR SYNTHESIS, AND METHODS OF USE THEREOF

(75) Inventors: Dong Wang, Omaha, NE (US); Xin-Ming Liu, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 1021 days.

(21) Appl. No.: 13/577,131

(22) PCT Filed: Feb. 7, 2011

(86) PCT No.: PCT/US2011/023897
§ 371 (c)(1),
(2), (4) Date: Sep. 11, 2012

(87) PCT Pub. No.: WO2011/097563
PCT Pub. Date: Aug. 11, 2011

(65) Prior Publication Data
US 2013/0004425 A1 Jan. 3, 2013

Related U.S. Application Data

(60) Provisional application No. 61/302,328, filed on Feb. 8, 2010.

(51) Int. Cl.
*A61K 47/48* (2006.01)
*A61K 9/127* (2006.01)
*A61K 31/431* (2006.01)
*A61K 33/16* (2006.01)

(52) U.S. Cl.
CPC ....... *A61K 47/48815* (2013.01); *A61K 9/1271* (2013.01); *A61K 9/1272* (2013.01); *A61K 31/431* (2013.01); *A61K 33/16* (2013.01); *A61K 47/48084* (2013.01)

(58) Field of Classification Search
CPC ............. A61K 9/127; A61K 47/48815
See application file for complete search history.

(56) References Cited

U.S. PATENT DOCUMENTS

| 4,767,615 A * | 8/1988 | Geho ........................ A61K 8/14 424/49 |
| 2007/0154537 A1* | 7/2007 | Greb ........................ A61K 9/127 424/450 |
| 2008/0159959 A1 | 7/2008 | Wang et al. |
| 2009/0068178 A1 | 3/2009 | Crowley et al. |
| 2009/0209493 A1 | 8/2009 | Baulch-Brown et al. |
| 2009/0311182 A1 | 12/2009 | Wang et al. |
| 2010/0022481 A1 | 1/2010 | Wang et al. |
| 2010/0047258 A1 | 2/2010 | Wang et al. |
| 2011/0171144 A1 | 7/2011 | Wang et al. |
| 2012/0189543 A1 | 7/2012 | Wang et al. |

FOREIGN PATENT DOCUMENTS

| CN | 1681515 A | 10/2005 |
| WO | 2008/137758 | 11/2008 |

OTHER PUBLICATIONS

Russell et al. (1999). "Bisphosphonates: From the Laboratory to the Clinic and Back Again." Bone, 25(1): 96-106.*
Liu et al. (2007). "Efficient Synthesis of Linear Multifunctional Poly(ethylene glycol) by Copper (I)-Catalyzed Huisgen 1,3-Dipolar Cycloaddition." Biomacromolecules, 8: 2653-2658.*
Liu, X-M., et al., "Novel Biomineral-Binding Cyclodextrins for Controlled Drug Delivery in the Oral Cavity" Journal of Controlled Release (2007) 122:54-62.
Chen, F., et al., "Tooth-Binding Micelles for Dental Caries Prevention" Antimicrobial Agents and Chemotherapy (2009) 53(11):4898-4902.

* cited by examiner

*Primary Examiner* — Frederick Krass
*Assistant Examiner* — Amanda Heyes
(74) *Attorney, Agent, or Firm* — Robert C. Netter, Jr.; Dann, Dorfman, Herrell & Skillman

(57) ABSTRACT

Drug carriers, methods of synthesizing, and methods of use thereof are provided. The drug carriers are liposomes comprising at least one functionalized cholesterol of the formula: Chol-X-T, wherein X is a linker domain, T is at least one targeting moiety which binds hard tissue and/or medical implants, and Chol is cholesterol or a derivative or analog thereof. The liposomes may encapsulate at least one therapeutic agent for the treatment of an oral disease or disorder.

9 Claims, 5 Drawing Sheets

US 9,545,452 B2

BIOMINERAL AND METAL BINDING LIPOSOMES, THEIR SYNTHESIS, AND METHODS OF USE THEREOF

This application is a §371 application of PCT/US2011/023897, filed Feb. 7, 2011, which claims priority under 35 U.S.C. §119(e) to U.S. Provisional Patent Application No. 61/302,328, filed on Feb. 8, 2010. The Entire disclosure of each of the foregoing applications is incorporated by reference herein.

This invention was made with government support under Grant No. AR053325 awarded by the National Institutes of Health. The Government has certain rights in this invention.

FIELD OF THE INVENTION

The present invention relates to drug carriers and methods of use thereof. More specifically, the instant invention relates to hard tissue and metal targeting liposomes.

BACKGROUND OF THE INVENTION

Several publications and patent documents are cited throughout the specification in order to describe the state of the art to which this invention pertains. Each of these citations is incorporated herein by reference as though set forth in full.

Hard tissues, including cartilage, tooth, and bone, and medical implants are hosts to a wide variety of disorders and diseases (e.g., dental caries, osteoporosis, bone cancer, and the like), which require the targeted delivery of therapeutic agents. Many therapeutic agents have been developed to treat these disorders and diseases. However, the success of these therapeutic agents has been largely limited by the inability to specifically deliver them to the target tissue at an effective and sustained concentration. The instant invention allows for the delivery of compounds, such as these therapeutic agents, in a targeted manner without the need for chemical modification of the delivered compounds.

SUMMARY OF THE INVENTION

In accordance with the instant invention, functionalized cholesterols of the formula: Chol-X-T, wherein X is a linker domain, T is at least one targeting moiety which binds hard tissue and/or medical implants, and Chol is cholesterol or a derivative or analog thereof, are provided. The instant invention also encompasses liposomes comprising at least one functionalized cholesterol. The liposomes may comprise/encapsulate at least one detectable agent and/or therapeutic agent.

In accordance with another aspect of the instant invention, PEGylated phospholipids of the formula: Phos-X-T, wherein X is a linker domain, T is at least one targeting moiety which binds hard tissue and/or medical implants, and Phos is a phospholipid or a derivative or analog thereof, are provided. The instant invention also encompasses liposomes comprising at least one PEGylated phospholipid. The liposomes may comprise/encapsulate at least one detectable agent and/or therapeutic agent.

According to yet another aspect of the instant invention, methods of synthesizing the liposomes, functionalized cholesterol, and the PEGylated phospholipids are provided.

In accordance with another aspect of the instant invention, methods of preventing, treating, or inhibiting a bone related disease or disorder and/or oral diseases or disorders are provided. In a particular embodiment, the methods comprise administering at least one liposome of the instant invention.

DETAILED DESCRIPTION OF THE INVENTION

Figure 1A:
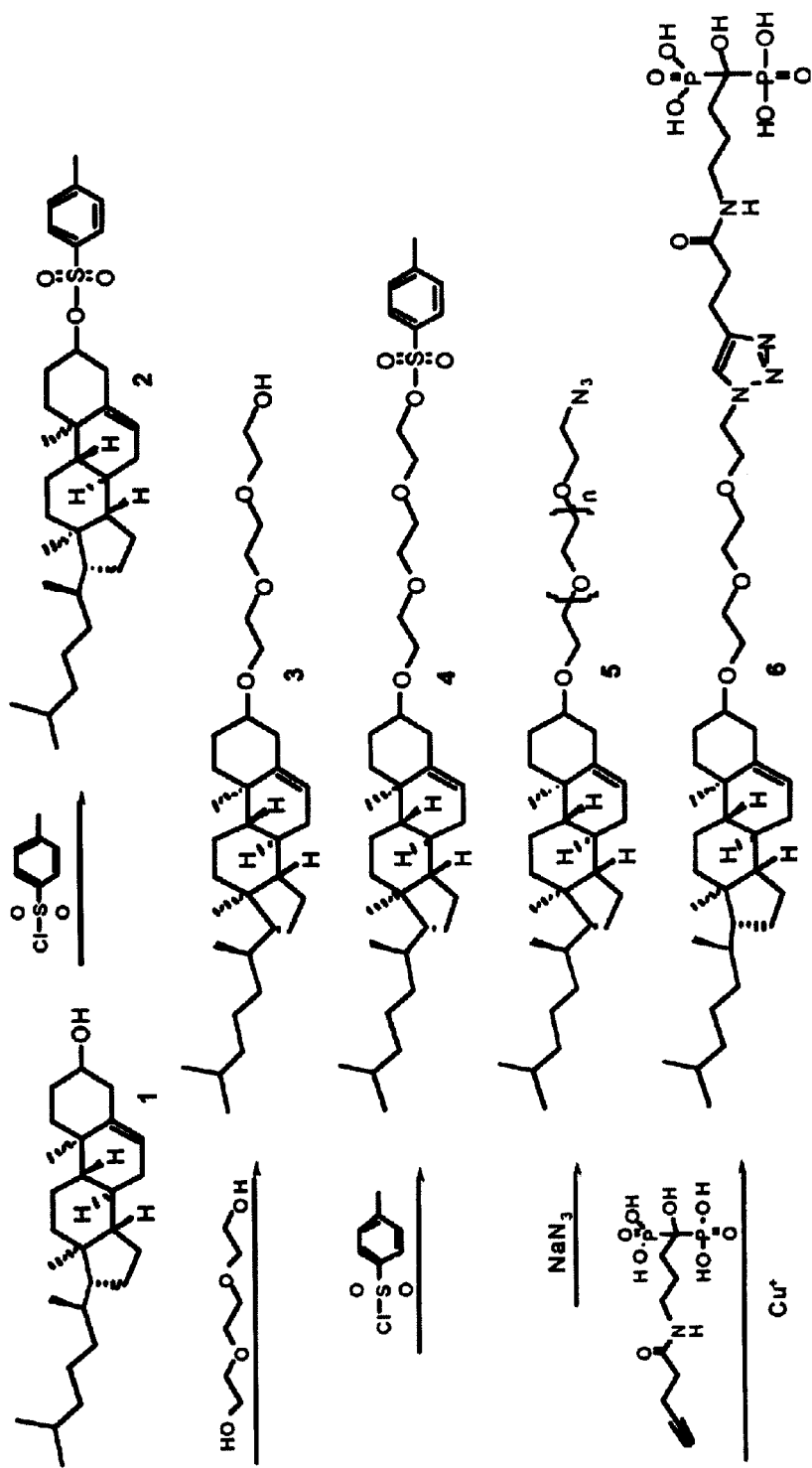
FIG. 1A provides a scheme for the synthesis of alendronate-triethylene glycol-cholesterol.

Biomineral and metal binding liposomes are encompassed by the instant invention. The liposomes of the instant invention efficiently bind to biominerals and other hard surfaces such as bone (e.g., joints), teeth, hydroxyapatite, calcium phosphate, medical implants (e.g., bone grafts, metal implants, stainless steel), and the like. The delivery-vehicles of the instant invention can encapsulate hydrophilic or hydrophobic compounds. The delivery vehicles can also encapsulate low molecular weight compounds (e.g., small chemical compounds, antimicrobials, anabolic agents) as well as large macromolecules (e.g., peptides, proteins, DNA, RNA, polysaccharide, synthetic polymers, and polymer conjugates). In a particular embodiment, the liposomes encapsulate at least one biologically active agent/compound. The liposomes of the instant invention can also be used as a local or systemic delivery platform to deliver imaging and/or therapeutic agents to a desired location (e.g., bone, the skeleton, tooth, or medical implants). Examples of therapeutic agents include, without limitation, small molecules, bone anabolic agents, enzyme inhibitors, angiogenesis promoting agents, antimicrobials, statins, BMPs, agents that interfere with Wnt signaling pathway, anticancer chemotherapeutic agents, and the like.

In a particular embodiment, the liposomes encapsulate fluoride or fluoride containing salts such as NaF. These liposomes can be used to deliver the fluoride to the tooth surface. Fluoride addition to drinking water has significantly improved dental health worldwide. However, it is a systemic approach that also exposes the skeleton to fluoride. Accordingly, a simple and culturally acceptable fluoride formulation is needed to deliver supplemental fluoride ions to the tooth surface for sustained period of time.

I. Liposomes

In one embodiment of the instant invention, liposomes which target biominerals, implants, metal, and hard tissue are provided. As stated hereinabove, the liposomes of the instant invention may comprise at least one imaging and/or therapeutic agent.

In one embodiment, the liposomes comprise at least one functionalized cholesterol. In a particular embodiment, the liposomes comprise at least one compound of the following formula: Chol-X-T, wherein X is a linker domain, T is a targeting moiety or moieties which binds hard tissue and/or medical implants, and Chol is cholesterol or a derivative or analog thereof.

The linker domain X is a chemical moiety comprising a covalent bond or a chain of atoms that covalently attaches the targeting moiety to the cholesterol. In a particular embodiment, the linker may contain from 0 (i.e., a bond) to about 500 atoms, about 1 to about 100 atoms, or about 1 to about 50 atoms. The linker can be linked to any synthetically feasible position of cholesterol. In a preferred embodiment the linker is attached at the —OH position of cholesterol. The linker may be biodegradable under physiological environments or conditions. The linker may also be non-degradable and may be a covalent bond or any other chemical structure which cannot be cleaved under physiological environments or conditions.

Exemplary linkers may comprise at least one optionally substituted; saturated or unsaturated; linear, branched or cyclic alkyl, alkenyl, or aryl group. The linker may also be a polypeptide (e.g., from about 1 to about 20 amino acids). In a particular embodiment, the linker is a polymer, copolymer, amphiphilic copolymer, or an amphiphilic block copolymer (e.g., an A-B-A block copolymer). In yet another embodiment, the linker is a polymer or a block copolymer comprising at least one ethylene oxide (EO) and/or propylene oxide (PO) segment (e.g., 1 to 10 EO or PO units per segment). In a particular embodiment, the linker is triethylene glycol.

Targeting moieties (T) are those compounds which preferentially accumulate in/on hard tissue (e.g., tooth and bone) and/or medical implants (e.g., bone graft/implant, hydroxyapatite-coated metal implant, metal implants such as stainless steel, titanium alloy, orthopedic implants, dental implants, and bone marrow grafts) rather than any other organ or tissue in vivo. Targeting moieties of the instant invention include, without limitation, folic acid, mannose, bisphosphonates (e.g., alendronate), tetracycline and its analogs, sialic acid, malonic acid, N,N-dicarboxymethylamine, 4-aminosalicyclic acid, 5-aminosalicyclic acid, antibodies or fragments or derivatives thereof specific for hard tissue or implant material (e.g., Fab, humanized antibodies, and/or single chain variable fragment (scFv)), and peptides (e.g., peptides comprising about 2 to about 100 (particularly 6) D-glutamic acid residues, L-glutamic acid residues, D-aspartic acid residues, L-aspartic acid residues, D-phosphoserine residues, L-phosphoserine residues, D-phosphothreonine residues, L-phosphothreonine residues, D-phosphotyrosine residues, and/or L-phosphotyrosine residues). In a particular embodiment, the targeting moiety is alendronate.

In a particular embodiment, the functionalized cholesterol is formed by reacting a compound of the formula:

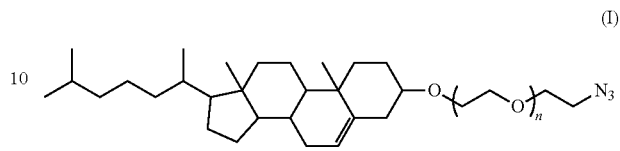

(I)

wherein n is 0 to about 100, 0 to about 10, 1 to about 5, or 1 to about 3, with a targeting moiety linked (e.g., via a linker domain (e.g., a lower alkyl)) to a HC≡C— group, via an azide-alkyne Huisgen cycloaddition reaction (see, e.g., FIG. 1A; Rostovtsev et al. (2002) Angew. Chem. Int. Ed., 41:2596-2599; Bock et al. (2006) Eur. J. Org. Chem., 51-68). In a particular embodiment, the compound of formula (I) is reacted with a compound having the formula:

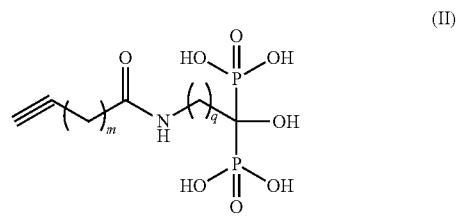

(II)

wherein m is 1 to about 10, 1 to about 5, or 1 to about 3 and wherein q is 1 to about 10, 1 to about 7, or 1 to about 5. Formula II depicts the targeting moiety as alendronate or a derivative thereof. As stated hereinabove, a compound of Formula I can be reacted with any targeting moiety linked to a HC≡C— group.

In another embodiment, the functionalized cholesterol has the formula:

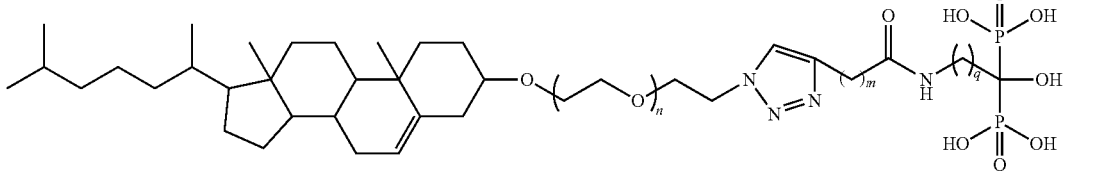

(III)

wherein n is 0 to about 100, 0 to about 10, 1 to about 5, or 1 to about 3; wherein m is 1 to about 10, 1 to about 5, or 1 to about 3; and q is 1 to about 10, 1 to about 7, or 1 to about 5. Formula III depicts the targeting moiety as alendronate, but other targeting moieties may be used.

In accordance with another aspect of the instant invention, the liposomes comprise at least one PEGylated phospholipid. In a particular embodiment, the liposomes comprise at least one compound of the following formula: Phos-X-T, wherein X is a linker domain, T is a targeting moiety or moieties which binds hard tissue and/or medical implants, and Phos is a phospholipid or a derivative or analog thereof. The targeting moiety and linker domain are as described hereinabove.

The term "phospholipids" generally refers to a molecule that includes a backbone (e.g., glycerol or sphingosine) attached to at least two fatty acid moieties and at least one phosphate group. Phospholipids can be natural or partially or wholly synthetic; of variable lipid chain length; and saturated or unsaturated. Phospholipids include, without limitation, phosphatidylcholines (PC; e.g., distearoylphosphatidylcholine (DSPC), hydrogenated soy phosphatidylcholine (HSPC), soy phosphatidylcholine (soy PC), egg phosphatidylcholine (egg PC), hydrogenated egg phosphatidylcholine (HEPC), dipalmitoylphosphatidylcholine (DPPC) and dimyristoylphosphatidylcholine (DMPC)); phosphatidylserines; phosphatidylglycerols (PG; dimyristoylphosphatidylglycerol (DMPG), dilaurylphosphatidylglycerol (DLPG), dipalmitoylphosphatidylglycerol (DPPG), distearoylphosphatidylglycerol (DSPG)); phosphatic acids (PA; dimyristoylphosphatidic acid (DMPA), distearoylphosphatidic acid (DSPA), dilaurylphosphatidic acid (DLPA), dipalmitoylphosphatidic acid (DPPA), and phosphatidic acids containing lauric, myristic, stearoyl, and palmitic acid chains); phosphatidylethanolamines (PE), phosphatidylinositols, and sphingomyelins.

Figure 1B:
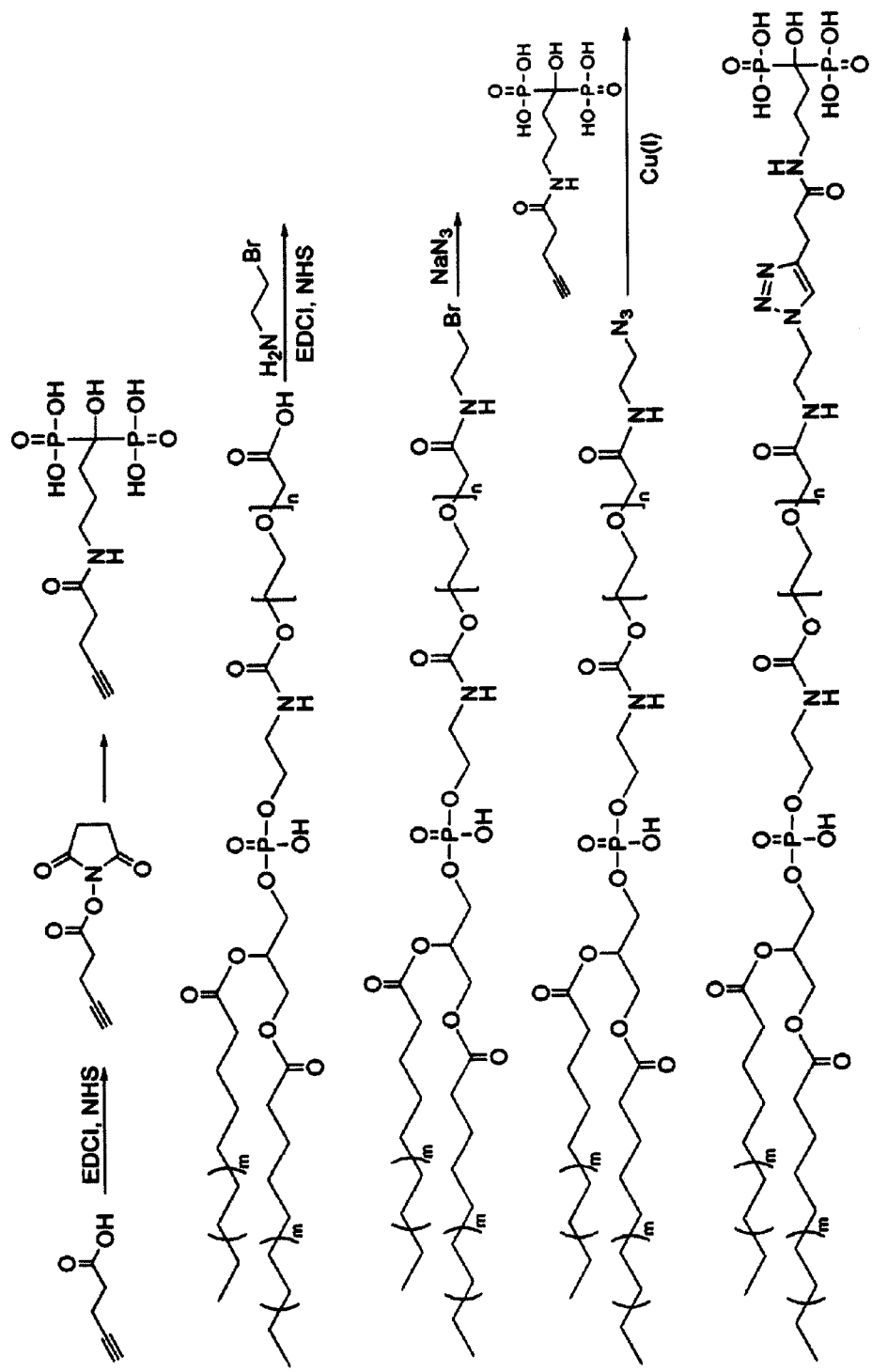
FIG. 1B provides a scheme for the synthesis of PEGylated phospholipids.
Figure 1C:
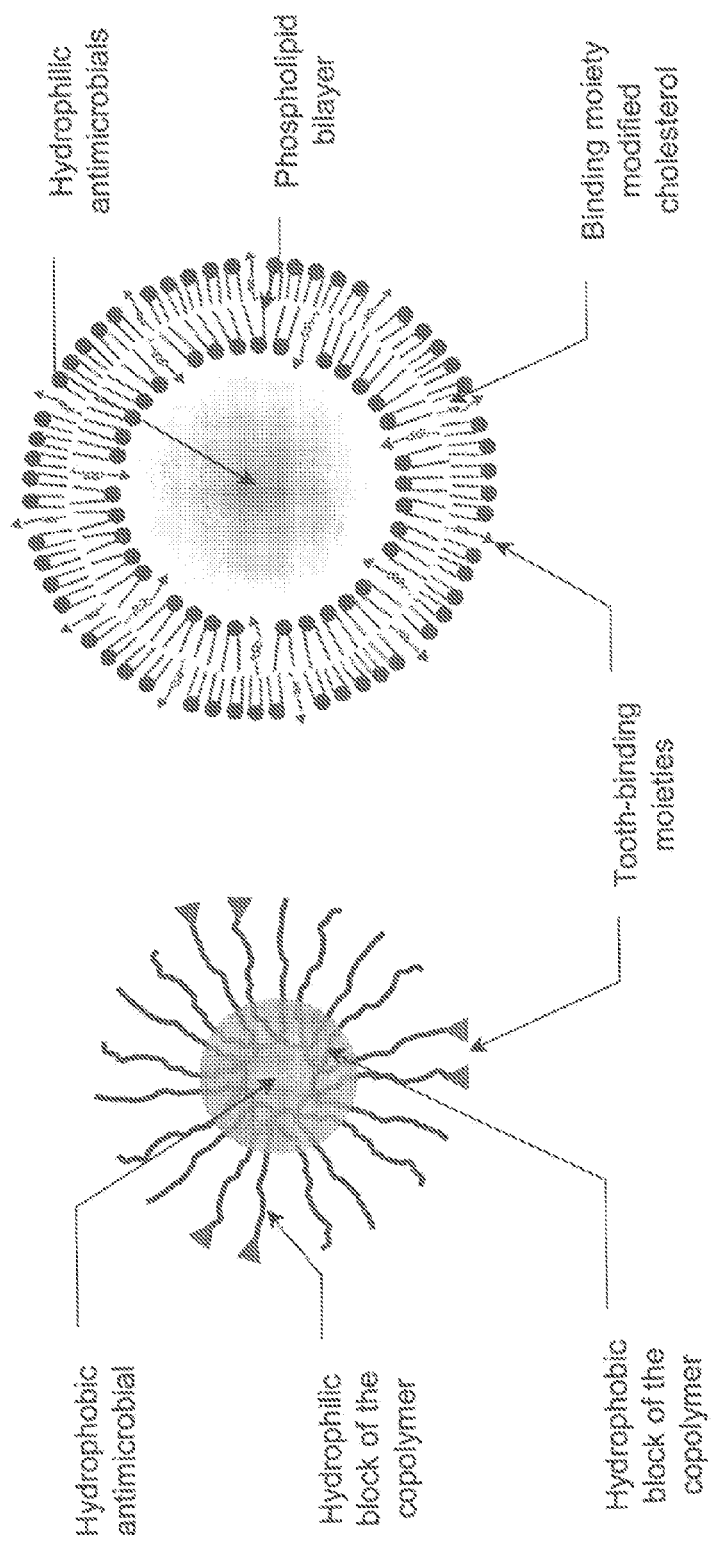
FIG. 1C provides a schematic of a biomineral-binding liposome containing three major components: biomineral-binding moiety modified cholesterol, phosphate lipid bilayer, and hydrophilic antimicrobial which is encapsulated in the center of the liposome.

In a particular embodiment, the PEGylated phospholipid is formed by reacting a compound of the formula:

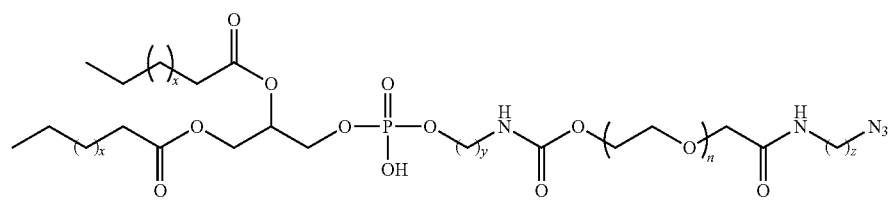

formula (IV) is reacted with a compound having the formula:

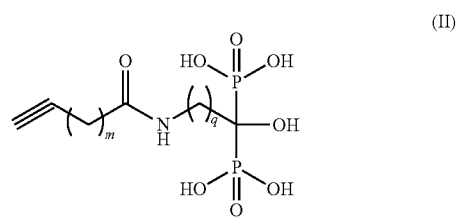

wherein m is 1 to about 10, 1 to about 5, or 1 to about 3 and wherein q is 1 to about 10, 1 to about 7, or 1 to about 5. Formula II depicts the targeting moiety as alendronate or a derivative thereof. As stated hereinabove, a compound of Formula IV can be reacted with any targeting moiety linked to a HC≡C— group.

wherein x is about 1 to about 30 or about 5 to about 20; wherein y is about 1 to about 10, 1 to about 5, or 1 to about 3; wherein n is 1 to about 100, 1 to about 10, 1 to about 5, or 1 to about 3; and wherein z is about 1 to about 10, 1 to about 5, or 1 to about 3, with a targeting moiety linked (e.g., via a linker domain (e.g., a lower alkyl)) to a HC≡C— group, via an azide-alkyne Huisgen cycloaddition reaction (see FIG. 1B). In a particular embodiment, the compound of In another embodiment, the PEGylated phospholipid has the formula:

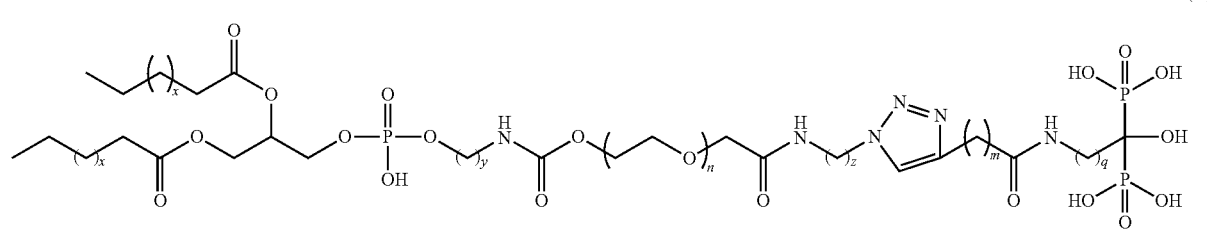

wherein x is about 1 to about 30 or about 5 to about 20; wherein y is about 1 to about 10, 1 to about 5, or 1 to about 3; wherein n is 1 to about 100, 1 to about 10, 1 to about 5, or 1 to about 3; wherein z is about 1 to about 10, 1 to about 5, or 1 to about 3; wherein m is 1 to about 10, 1 to about 5, or 1 to about 3; and wherein q is 1 to about 10, 1 to about 7, or 1 to about 5. Formula V depicts the targeting moiety as alendronate, but other targeting moieties may be used.

The liposomes of the instant invention may be comprised solely of the above functionalized cholesterols and/or PEGylated phospholipids. The liposomes may also solely comprise one or more functionalized cholesterol or solely comprise one or more PEGylated phospholipid. In yet another embodiment, the liposomes may comprise any other liposome forming compounds (e.g., amphiphilic molecules, lipids, phospholipids, etc.). The liposomes may also comprise cholesterol. The liposomes may also comprise hydrophobic dyes incorporated into the lipid membrane. The functionalized cholesterols and/or PEGylated phospholipids of the instant invention may comprise any percentage of the liposome-forming compounds present in the liposome. For example, the functionalized cholesterols and/or PEGylated phospholipids of the instant invention may comprise from about 1% or less of the liposome to 99% or more of the liposome. In a particular embodiment, the functionalized cholesterols and/or PEGylated phospholipids comprise 1% to 50% of the liposome (e.g., by weight). In a particular embodiment, the functionalized cholesterols and/or PEGylated phospholipids are present in the liposomes at a concentration high enough to promote targeting of the liposomes to the desired target (e.g., without a significant drop off from levels with liposomes comprising only the functionalized cholesterols and/or PEGylated phospholipid).

As stated hereinabove, liposomes of the instant invention may encompass at least one compound of interest. In a particular embodiment, the liposomes encompass at least one detectable agent and/or therapeutic agent. Examples of therapeutic agents include, without limitation, fluoride or fluoride containing salts (e.g., NaF), small molecules, bone related therapeutic agents, bone anabolic agents, enzyme inhibitors, angiogenesis promoting agents (e.g., prostaglandin E1 or E2), antimicrobials, statins, BMPs, peptides, proteins, nucleic acids (e.g., DNA, RNA, siRNA, antisense), polysaccharides, synthetic polymers, polymer conjugates agents that interfere with Wnt signaling pathway (e.g., sclerostin antibodies), and chemotherapeutic agents.

A "bone related therapeutic agent" refers to an agent suitable for administration to a patient that induces a desired biological or pharmacological effect such as, without limitation, 1) increasing bone growth, 2) preventing an undesired biological effect such as an infection, 3) alleviating a condition (e.g., pain or inflammation) caused by a disease associated with bone, and/or 4) alleviating, reducing, or eliminating a disease from bone. In a particular embodiment, the bone related therapeutic agent possesses a bone anabolic effect and/or bone stabilizing effect. Bone related therapeutic agents include, without limitation, cathepsin K inhibitor, metalloproteinase inhibitor, prostaglandin E receptor agonist, prostaglandin E1 or E2 and analogs thereof, parathyroid hormone and fragments thereof, resolvins and analogs thereof, antimicrobials, glucocorticoids (e.g., dexamethasone) and derivatives thereof, and statins (e.g., simvastatin).

Detectable agents include, without limitation, imaging agent, optical imaging agent (e.g., phorphyrins, anthraquinones, anthrapyrazoles, perylenequinones, xanthenes, cyanines, acridines, phenoxazines, phenothiazines and derivatives thereof), contrast agent (e.g., MRI contrast agent), gold (e.g., gold particles or gold nanoparticles), isotope, radioisotope, fluorescent agents (e.g., fluorescein and rhodamine and their derivatives, DiI, and DiO), and paramagnetic or superparamagnetic ions (e.g., Gd(III), Eu(III), Dy(III), Pr(III), Pa(IV), Mn(II), Cr(III), Co(III), Fe(III), Cu(II), Ni(II), Ti(III), and V(IV)) (examples of other labels are provided in, for example, U.S. Pat. Nos. 3,817,837; 3,850,752; 3,939,350; 3,996,345; 4,277,437; 4,275,149 and 4,366,241).

Chemotherapeutic agents are compounds that exhibit anticancer activity and/or are detrimental to a cell (e.g., a toxin). Suitable chemotherapeutic agents include, but are not limited to: toxins (e.g., saporin, ricin, abrin, ethidium bromide, diptheria toxin, and *Pseudomonas* exotoxin); taxanes; alkylating agents (e.g., nitrogen mustards such as chlorambucil, cyclophosphamide, isofamide, mechlorethamine, melphalan, and uracil mustard; aziridines such as thiotepa; methanesulphonate esters such as busulfan; nitroso ureas such as carmustine, lomustine, and streptozocin; platinum complexes (e.g., cisplatin, carboplatin, tetraplatin, ormaplatin, thioplatin, satraplatin, nedaplatin, oxaliplatin, heptaplatin, iproplatin, transplatin, and lobaplatin); bioreductive alkylators such as mitomycin, procarbazine, dacarbazine and altretamine); DNA strand-breakage agents (e.g., bleomycin); topoisomerase II inhibitors (e.g., amsacrine, menogaril, amonafide, dactinomycin, daunorubicin, N,N-dibenzyl daunomycin, ellipticine, daunomycin, pyrazoloacridine, idarubicin, mitoxantrone, m-AMSA, bisantrene, doxorubicin (adriamycin), deoxydoxorubicin, etoposide (VP-16), etoposide phosphate, oxanthrazole, rubidazone, epirubicin, bleomycin, and teniposide); DNA minor groove binding agents (e.g., plicamydin); antimetabolites (e.g., folate antagonists such as methotrexate and trimetrexate); pyrimidine antagonists such as fluorouracil, fluorodeoxyuridine, CB3717, azacitidine, cytarabine, and floxuridine; purine antagonists such as mercaptopurine, 6-thioguanine, fludarabine, pentostatin; asparginase; and ribonucleotide reductase inhibitors such as hydroxyurea); and tubulin interactive agents (e.g., vincristine, vinblastine, and paclitaxel (Taxol®)).

Antimicrobials include, without limitation, farnesol, chlorhexidine (chlorhexidine gluconate), apigenin, triclosan, ceragenin CSA-13, and antibiotics. Antibiotics include, without limitation, beta-lactams (e.g., penicillin, ampicillin, oxacillin, cloxacillin, methicillin, and cephalosporin), carbacephems, cephamycins, carbapenems, monobactams, aminoglycosides (e.g., gentamycin, tobramycin), glycopeptides (e.g., vancomycin), quinolones (e.g., ciprofloxacin), moenomycin, tetracyclines, macrolides (e.g., erythromycin), fluoroquinolones, oxazolidinones (e.g., linezolid), lipopetides (e.g., daptomycin), aminocoumarin (e.g., novobiocin), co-trimoxazole (e.g., trimethoprim and sulfamethoxazole), lincosamides (e.g., clindamycin and lincomycin), metronidazole, polypeptides (e.g., colistin), and derivatives thereof.

Compositions comprising the hard tissue/medical implant targeting liposomes are also encompassed by the instant invention. The compositions comprise the liposomes and at least one pharmaceutically acceptable carrier. In addition to the agents encapsulated by the liposomes, the composition may also further comprise at least one antibiotic, anti-inflammatory drug, anesthetic, and/or "bone related therapeutic agent."

The pharmaceutical compositions of the present invention can be administered by any suitable route, for example, by injection, oral, pulmonary, or other modes of administration. The compositions of the instant invention may be administered locally or systemically (e.g., for treating osteoporosis). In a particular embodiment, the composition is injected directly to the desired site.

The pharmaceutical compositions of the present invention may be delivered in a controlled release system, such as via an implantable osmotic pump or other mode of administration. In another embodiment, polymeric materials may be employed to control release (see Medical Applications of Controlled Release, Langer and Wise (eds.), CRC Press: Boca Raton, Fla. (1974); Controlled Drug Bioavailability, Drug Product Design and Performance, Smolen and Ball (eds.), Wiley: New York (1984); Ranger and Peppas, J. Macromol. Sci. Rev. Macromol. Chem. (1983) 23:61; see also Levy et al., Science (1985) 228:190; During et al., Ann. Neurol. (1989) 25:351; Howard et al., J. Neurosurg. (1989) 71:105). The controlled release system may be placed in proximity of the target area of the subject. Other potential controlled release systems are discussed in the review by Langer (Science (1990) 249:1527 1533).

Compositions of the instant invention may also be administered as part of a medical device. As used herein, the term "medical device" includes devices and materials that are permanently implanted and those that are temporarily or transiently present in the patient. The compositions of the invention can be released from the medical devices or coated on the medical devices. Medical devices include, without limitation, stents, plates, fracture implants, gels, polymers (e.g., sustained release polymers or gels), and release devices.

The compositions of the invention may also be coated on or administered with grafts and implants such as, without limitation, dura mater grafts, cartilage grafts, cartilage implants, bone grafts, bone implants, orthopedic implants, dental implants, and bone marrow grafts.

The present invention is also directed to methods of preventing, inhibiting, or treating bone disorders and bone disorder-related conditions or complications in a subject that is in need of such prevention or treatment, comprising administering to the patient a composition of the instant invention. Bone disorders may be associated with bone loss and include, without limitation, bone cancer, osteoporosis, osteopenia, bone fractures, bone breaks, Paget's disease (osteitis deformans), bone degradation, bone weakening, skeletal distortion, low bone mineral density, scoliosis, osteomalacia, osteomyelitis, osteogenesis imperfecta, osteopetrosis, enchondromatosis, osteochondromatosis, achondroplasia, alveolar bone defects, spine vertebra compression, bone loss after spinal cord injury, avascular necrosis, fibrous dysplasia, periodontal disease, hyperparathyroidism (osteitis fibrosa cystica), hypophosphatasia, fibrodysplasia ossificans progressive, and pain and inflammation of the bone. Bone related therapeutic agents can be administered in the same composition as the liposomes of the instant invention or may be administered in a separate composition either concurrently or at a different time.

The compositions of the instant invention may also be used to treat and/or inhibit oral diseases and disorders. Oral disease and disorders include, without limitation, caries, gingivitis, periodontitis, periodontitis-associated bone loss, dentin hypersensitivity, oral mucosal disease, oral mucositis, vesiculo-erosive oral mucosal disease, stained/discolored teeth, dry mouth, and halitosis. In a particular embodiment, the encapsulated compound is an antimicrobial, anti-inflammatory, menthol, a fragrant agent (e.g., limonene, orange oil), a flavoring agent, cooling agent, fluoride, vitamins, neutraceuticals, tooth whitening agents, tooth coloring agents, bleaching or oxidizing agents, thickening agents, and sweetening agents. Examples of such agents can be found, for example, in U.S. Patent Application Publication No. 2006/0286044 and PCT/EP2005/009724.

The liposomes of the instant invention may also be used to treat or inhibit arthritis. For example, the liposomes may encapsulate anti-inflammatory compounds and/or immuno- suppressive agents (nonsteroidal anti-inflammatory drugs (NSAIDs), glucocorticosteroids (GC), and disease-modifying antirheumatic drugs (DMARDs)) to deliver to sites of joint inflammation in patients with inflammatory arthritis.

II. Definitions

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "isolated" refers to the separation of a compound from other components present during its production. "Isolated" is not meant to exclude artificial or synthetic mixtures with other compounds or materials, or the presence of impurities that do not substantially interfere with the fundamental activity, and that may be present, for example, due to incomplete purification, or the addition of stabilizers.

"Linker", "linker domain", and "linkage" refer to a chemical moiety comprising a covalent bond or a chain of atoms that covalently attaches, for example, a targeting moiety to a cholesterol or a phospholipid. In various embodiments, a linker is specified as X. The linker can be linked to any synthetically feasible position of the compounds to be linked, but preferably such that the intended activity of the compounds is not significantly altered. Linkers are generally known in the art.

As used herein, the term "bone-targeting" refers to the capability of preferentially accumulating in hard tissue rather than any other organ or tissue, after administration in vivo.

As used herein, the term "biodegradable" or "biodegradation" is defined as the conversion of materials into less complex intermediates or end products by solubilization hydrolysis under physiological conditions, or by the action of biologically formed entities which can be enzymes or other products of the organism. The term "non-degradable" refers to a chemical structure that cannot be cleaved under physiological condition, even with any external intervention. The term "degradable" refers to the ability of a chemical structure to be cleaved via physical (such as ultrasonication), chemical (such as pH of less than 4 or more than 9) or biological (enzymatic) means.

A "therapeutically effective amount" of a compound or a pharmaceutical composition refers to an amount effective to prevent, inhibit, or treat the symptoms of a particular disorder or disease. For example, "therapeutically effective amount" may refer to an amount sufficient to modulate bone loss or osteoporosis in an animal, especially a human, including, without limitation, decreasing or preventing bone loss or increasing bone mass.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. The compositions can be incorporated into particulate preparations of polymeric compounds such as polylactic acid, polyglycolic acid, etc., or into liposomes or micelles. Such compositions may influence the physical state, stability, rate of in vivo release, and rate of in vivo clearance of components of a pharmaceutical composition of the present invention. The pharmaceutical composition of the present invention can be prepared, for example, in liquid form, or can be in dried powder form (e.g., lyophilized). Suitable pharmaceutical carriers are described in "Remington's Pharmaceutical Sciences" by E. W. Martin (Mack Publishing Co., Easton, Pa.); Gennaro, A. R., Remington: The Science and Practice of Pharmacy, 21st Edition, (Lippincott, Williams and Wilkins), 2005; Liberman, et al., Eds., Pharmaceutical Dosage Forms, Marcel Decker, New York, N.Y., 1980; and Kibbe, et al., Eds., Handbook of Pharmaceutical Excipients (3rd Ed.), American Pharmaceutical Association, Washington, 1999.

As used herein, the term "PEGylated" generally refers to having covalently attached at least one polyethylene glycol (PEG), particularly a polymer of PEG, to another molecule.

The term "alkyl," as employed herein, includes both straight and branched chain hydrocarbons containing about 1 to 20 carbons or about 5 to 15 carbons in the normal chain. The hydrocarbon chain of the alkyl groups may be interrupted with oxygen, nitrogen, or sulfur atoms. Examples of suitable alkyl groups include methyl, ethyl, propyl, isopropyl, butyl, t-butyl, isobutyl, pentyl, hexyl, isohexyl, heptyl, 4,4 dimethylpentyl, octyl, 2,2,4 trimethylpentyl, nonyl, decyl, the various branched chain isomers thereof, and the like. Each alkyl group may optionally be substituted with 1 to 4 substituents which include, for example, alkyl, halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)-$ or $NHRC(=O)-$, wherein R is an alkyl), urea ($-NHCONH_2$), alkylurea, aryl, ether, ester, thioester, nitrile, nitro, amide, carbonyl, carboxylate and thiol. The term "lower alkyl" refers to an alkyl which contains 1 to 4 carbons and/or heteroatoms in the hydrocarbon chain.

The term "cyclic alkyl" or "cycloalkyl," as employed herein, includes cyclic hydrocarbon groups containing 1 to 3 rings which may be fused or unfused. Cycloalkyl groups may contain a total of 3 to 20 carbons forming the ring(s), preferably 6 to 10 carbons forming the ring(s). Optionally, one of the rings may be an aromatic ring as described below for aryl. Cycloalkyl groups may contain one or more double bonds. The cycloalkyl groups may also optionally contain substituted rings that includes at least one, and preferably from 1 to about 4 sulfur, oxygen, or nitrogen heteroatom ring members. Each cycloalkyl group may be optionally substituted with 1 to about 4 substituents such as alkyl (an optionally substituted straight, branched or cyclic hydrocarbon group, optionally saturated, having from about 1-10 carbons, particularly about 1-4 carbons), halo (such as F, Cl, Br, I), haloalkyl (e.g., $CCl_3$ or $CF_3$), alkoxyl, alkylthio, hydroxy, methoxy, carboxyl, oxo, epoxy, alkyloxycarbonyl, alkylcarbonyloxy, amino, carbamoyl (e.g., $NH_2C(=O)-$ or $NHRC(=O)-$, wherein R is an alkyl), urea ($-NHCONH_2$), alkylurea, aryl, ether, ester, thioester, nitrile, nitro, amide, carbonyl, carboxylate and thiol.

"Alkenyl" refers to an unsubstituted or substituted hydrocarbon moiety comprising one or more carbon to carbon double bonds (i.e., the alkenyl group is unsaturated) and containing from about 2 to about 20 carbon atoms or from about 5 to about 15 carbon atoms, which may be a straight, branched, or cyclic hydrocarbon group. When substituted, alkenyl groups may be substituted at any available point of attachment. Exemplary substituents may include, but are not limited to, alkyl, halo, haloalkyl, alkoxyl, alkylthio, hydroxyl, methoxy, carboxyl, oxo, epoxy, alkyloxycarbonyl, alkylcarbonyloxy, amino, carbamoyl, urea, alkylurea, and thiol. In a particular embodiment, the alkenyl group comprises alternating double and single bonds such that bonds are conjugated.

The term "aryl," as employed herein, refers to monocyclic and bicyclic aromatic groups containing 6 to 10 carbons in the ring portion. Examples of aryl groups include, without limitation, phenyl, naphthyl, such as 1-naphthyl and 2-naphthyl, indolyl, and pyridyl, such as 3-pyridyl and 4-pyridyl. Aryl groups may be optionally substituted through available carbon atoms with 1 to about 4 groups. Exemplary substituents may include, but are not limited to, alkyl, halo, haloalkyl, alkoxyl, alkylthio, hydroxyl, methoxy, carboxyl, carboxylate, oxo, ether, ester, epoxy, alkyloxycarbonyl, alkylcarbonyloxy, amino, carbamoyl, urea, alkylurea, thioester, amide, nitro, carbonyl, and thiol. The aromatic groups may be heteroaryl. "Heteroaryl" refers to an optionally substituted aromatic ring system that includes at least one, and preferably from 1 to about 4 sulfur, oxygen, or nitrogen heteroatom ring members.

"Polyethylene glycol," "PEG," and "poly(ethylene glycol)," as used herein, refer to compounds of the structure "—$(OCH_2CH_2)_n$—" where (n) ranges from 2 to about 4000. The PEGs of the instant invention may have various terminal or "end capping" groups. The PEGs may be "branched" or "forked", but are preferably "linear."

The following examples are provided to illustrate various embodiments of the present invention. They are not intended to limit the invention in any way.

Example 1

Synthesis of cholest-5-en-3β-yloxy-tosylate (2)

To an ice-cooled solution of cholesterol (1) (1.933 g, 5 mmol) and triethyl amine (1.125 mL, 7.5 mmol) in 40 mL dry DCM, p-toluenesulfonylchloride (1.43 g, 7.5 mmol) was slowed added at 0° C. with DMAP (60 mg, 0.5 mmol) as the catalyst (see FIG. 1A). The reaction mixture was then allowed to stir at room temperature overnight. The reaction mixture was washed with 1 N HCl (2×40 ml), and brine (2×40 ml); the organic layer was separated and dried over anhydrous $Na_2SO_4$. The solvent was evaporated under vacuum. The crude product was purified with silica gel chromatography (Hexane/Chloroform 4:1). Yield: 2.32 g. $^1$H NMR ($CDCl_3$, 500 MHz) δ (ppm) 7.80 (d, 2H, J=7.8 Hz), 7.33 (d, 2H, J=8.3 Hz), 5.30 (d, 1H, J=4.9 Hz), 4.34-4.30 (m, 1H), 2.44 (s, 3H), 2.44-2.41 (m, 1H), 2.28-2.25 (m, 1H), 2.00-0.98 (m, 26 H), 0.96 (s, 3H), 0.90 (d, 3H, J=6.3 Hz), 0.86 (dd, 6H, $J_1$=6.3 Hz, $J_2$=2.2 Hz), 0.65 (s, 3H); $^{13}$C NMR ($CDCl_3$, 125 MHz) δ (ppm) 144.4, 138.8, 134.6, 129.7, 127.6, 123.5, 82.4, 56.6, 56.0, 49.9, 42.2, 39.6, 39.5, 38.8, 36.8, 36.3, 36.1, 35.7, 31.8, 31.7, 28.6, 28.2, 28.0, 24.2, 23.8, 22.8, 22.5, 21.6, 20.9, 19.1, 18.7, 11.8.

Synthesis of 8-(cholest-5-en-3β-yloxy)-3,6-dioxaoctan-1-ol (3)

To a solution of cholesteryl tosylate (2) (2.16 g, 4 mmol) in dry 1,4-dioxane (30 ml) was added tri(ethyleneglycol) (15 ml, 111 mmol). The mixture was refluxed for 6 hours under an Ar atmosphere. After concentration of the reaction mixture, it was dissolved in 50 mL chloroform. Then the solution was washed with saturated NaHCO₃ aqueous solution (2×50 ml), brine (2×50 ml), dried over anhydrous Na₂SO₄, and concentrated under vacuum to give crude product. The crude product was further purified with silica gel chromatography (Hexane/Ethyl acetate 2:1). The compound was obtained as a white oily solid. Yield: 580 mg. $^1$H NMR (CDCl₃, 500 MHz) δ (ppm) 5.34 (d, 1H, J=4.9 Hz), 3.76-3.60 (m, 12H), 3.21-3.16 (m, 1H), 2.79 (m, 1H), 2.39-2.36 (m, 1H), 2.24-2.19 (m, 1H), 2.05-1.01 (m, 25H), 0.99 (s, 3H), 0.91 (d, 3H, J=6.3 Hz), 0.86 (dd, 6H, J1=6.3 Hz, J2=2.2 Hz), 0.67 (s, 3H); $^{13}$C NMR (CDCl₃, 125 MHz) δ (ppm) 140.8, 121.5, 79.5, 72.6, 70.8, 70.5, 70.3, 67.1, 61.6, 56.7, 56.1, 50.1, 42.2, 39.7, 39.4, 38.9, 37.1, 36.8, 36.1, 35.7, 31.9, 31.8, 28.2, 28.1, 27.9, 24.2, 23.7, 22.8, 22.25, 21.0, 19.3, 18.6, 11.8.

Synthesis of 8-(cholest-5-en-3β-yloxy)-3,6-dioxaoctanyl tosylate (4)

To an ice-cooled solution of 8-(cholest-5-en-3β-yloxy)-3,6-dioxaoctan-1-ol (3) (518 mg, 1 mmol) and triethyl amine (0.2 mL, 1.3 mmol) in 10 mL dry DCM, p-toluenesulfonylchloride (248 mg, 1.3 mmol) was slowed added at 0° C. with DMAP (12 mg, 0.1 mmol) as the catalyst. The reaction mixture was then allowed to stir at room temperature overnight. The reaction mixture was washed with 1 N HCl (2×10 ml), and brine (2×10 ml); the organic layer was separated and dried over anhydrous Na₂SO₄. The solvent was evaporated under vacuum. The crude product was purified with silica gel chromatography (Hexane/Chloroform 4:1). Yield: 570 mg. $^1$H NMR (CDCl₃, 500 MHz) δ (ppm) 7.80 (d, 2H, J=8.3 Hz), 7.34 (d, 2H, J=7.8 Hz), 5.34 (d, 1H, J=4.9 Hz), 4.16 (t, 2H, J=4.9 Hz), 3.69 (t, 2H, J=4.9 Hz), 3.61-3.59 (m, 8H), 3.18-3.15 (m, 1H), 2.45 (s, 3H), 2.37-2.34 (m, 1H), 2.22-2.19 (m, 1H), 2.02-1.01 (m, 26H), 0.99 (s, 3H), 0.91 (d, 3H, J=6.3 Hz), 0.86 (dd, 6H, J₁=6.3 Hz, J₂=2.2 Hz), 0.67 (s, 3H); $^{13}$C NMR (CDCl₃, 125 MHz) δ (ppm) 144.7, 140.9, 132.9, 129.8, 127.9, 121.5, 79.4, 70.9, 70.7, 70.5, 69.2, 68.6, 67.2, 56.7, 56.1, 50.1, 42.3, 39.7, 39.5, 39.0, 37.2, 36.8, 36.1, 35.7, 31.9, 31.8, 28.3, 28.2, 28.0, 24.2, 23.8, 22.8, 22.5, 21.6, 21.0, 19.3, 18.7, 11.8.

Synthesis of 8-(cholest-5-en-3β-yloxy)-3,6-dioxaoctanyl azide (5)

8-(Cholest-5-en-3β-yloxy)-3,6-dioxaoctanyl tosylate (4) (337 mg, 0.5 mmol) was suspended in ethanol (5 mL), then sodium azide (325 mg, 5 mmol) was added. The reaction was carried out with reflux overnight. After being cooled to room temperature, the solution was concentrated then dissolved in 10 mL chloroform. The solution was washed with saturated NaHCO₃ aqueous solution (2×50 ml), brine (2×50 ml), dried over anhydrous Na₂SO₄, and concentrated under vacuum to give an oily product. $^1$H NMR (CDCl₃, 500 MHz) δ (ppm) 5.34 (d, 1H, J=4.9 Hz), 3.69-3.64 (m, 10H), 3.39 (t, 2H, J=4.9 Hz), 3.22-3.15 (m, 1H), 2.40-2.34 (m, 1H), 2.25-2.18 (m, 1H), 2.04-1.01 (m, 26H), 0.99 (s, 3H), 0.91 (d, 3H, J=6.3 Hz), 0.86 (dd, 6H, J₁=6.3 Hz, J₂=2.2 Hz), 0.67 (s, 3H); $^{13}$C NMR (CDCl₃, 125 MHz) δ (ppm) 140.9, 121.5, 79.4, 70.9, 70.7, 70.6, 70.0, 67.3, 56.7, 56.1, 50.6, 50.1, 42.3, 39.7, 39.5, 39.0, 37.2, 36.8, 36.1, 35.7, 31.9, 31.8, 28.3, 28.2, 28.0, 24.2, 23.8, 22.8, 22.5, 21.0, 19.3, 18.7, 11.8.

Synthesis of 8-(cholest-5-en-3β-yloxy)-3,6-dioxaoctanyl alendronate (6)

8-(Cholest-5-en-3β-yloxy)-3,6-dioxaoctanyl azide (5) (120 mg, 0.22 mmol) and 4.05 g (80 mg, 0.2 mmol) 1-hydroxy-4-pent-4-ynamidobutane-1,1-diyldiphosphonic acid were dissolved in THF/water (2 mL). CuSO₄.5H₂O (5 mg, 0.02 mmol) and stabilizing agent (8.7 mg, 0.02 mmol) were dissolved in 0.5 ml THF/water, then sodium ascorbate (40 mg, 0.2 mmol) in 0.5 mL THF/water was slowly added into copper solution under argon to produce catalyst solution, which was finally added dropwise (3.96 g, 20 mmol) into the reaction solution under argon. The reaction mixture was allowed to stir for 3 days at room temperature. The reaction solution was then precipitated into methanol for three times. Yield: 87 mg. $^1$H NMR (D₂O, 500 MHz) δ (ppm) 7.81 (s, 1H), 5.33 (s, 1H), 4.53 (s, 2H), 3.90 (s, 2H), 3.63-3.57 (m, 8H), 3.36 (m, 1H), 3.16 (s, 2H), 2.97 (s, 2H), 2.61 (s, 2H), 2.34-0.97 (m, 38H), 0.88 (d, 6H, J=6.3 Hz), 0.65 (s, 3H).

Preparation of Biomineral-Binding Liposomes

The standard sonication method was used to prepare small unilamellar liposomes (SUV). Briefly, for preparation of biomineral-binding liposomes, egg phosohatidvlcholine (50 mg), cholesterol (20 mg), ALN-TEG-Chol (10 mg), and fluorescence (5 mg, represent hydrophobic compound), or rhodamine B (5 mg, represent hydrophilic compound), or β-carotene (5 mg, represent hydrophobic compound with poor solubility), or fluorescene labeled HPMA copolymer (5 mg, represent water-soluble macromolecules) were dissolved in CHCl₃/methanol (4 mL). The lipid solutions were transferred into flasks and dried by evaporation under nitrogen stream. The samples were then stored under vacuum for 4 hours at 4° C. The thin lipid film formed on the wall of flask was hydrated with a phosphate-buffered saline solution (PBS, pH 7.4, 3 mL) and sonicated under nitrogen for 5 minutes (30 seconds on and 30 seconds off for each cycle) with a probe sonicator. Subsequent centrifugation with 10,000 rpm and purification with Sephadex® G-25 were carried out to remove untrapped dye and polymer.

Liposome Size Distribution

The purified liposomes were filtered with 0.2 μm filter and then subjected to effective hydrodynamic diameter ($D_{eff}$) measurements (Table 1)

TABLE 1

Size distribution of different liposomes

| | $D_{eff}$ | PDI |
|---|---|---|
| Biomineral-binding liposomes loaded with Rhodamine B | 142.1 ± 2.8 | 0.28 ± 0.01 |
| Conventional liposomes loaded with Rhodamine B | 105.4 ± 2.3 | 0.23 ± 0.02 |
| Biomineral-binding liposomes loaded with β-carotene | 88.5 ± 1.5 | 0.27 ± 0.01 |
| Conventional liposomes loaded with β-carotene | 135.1 ± 3.7 | 0.28 ± 0.02 |
| Biomineral-binding liposomes loaded with HPMA copolymer | 146.1 ± 1.2 | 0.31 ± 0.01 |
| Conventional liposomes loaded with HPMA copolymer | 186.0 ± 3.5 | 0.25 ± 0.02 |

Binding Ability of Biomineral-Binding Liposomes on HA Particles

Figure 2:
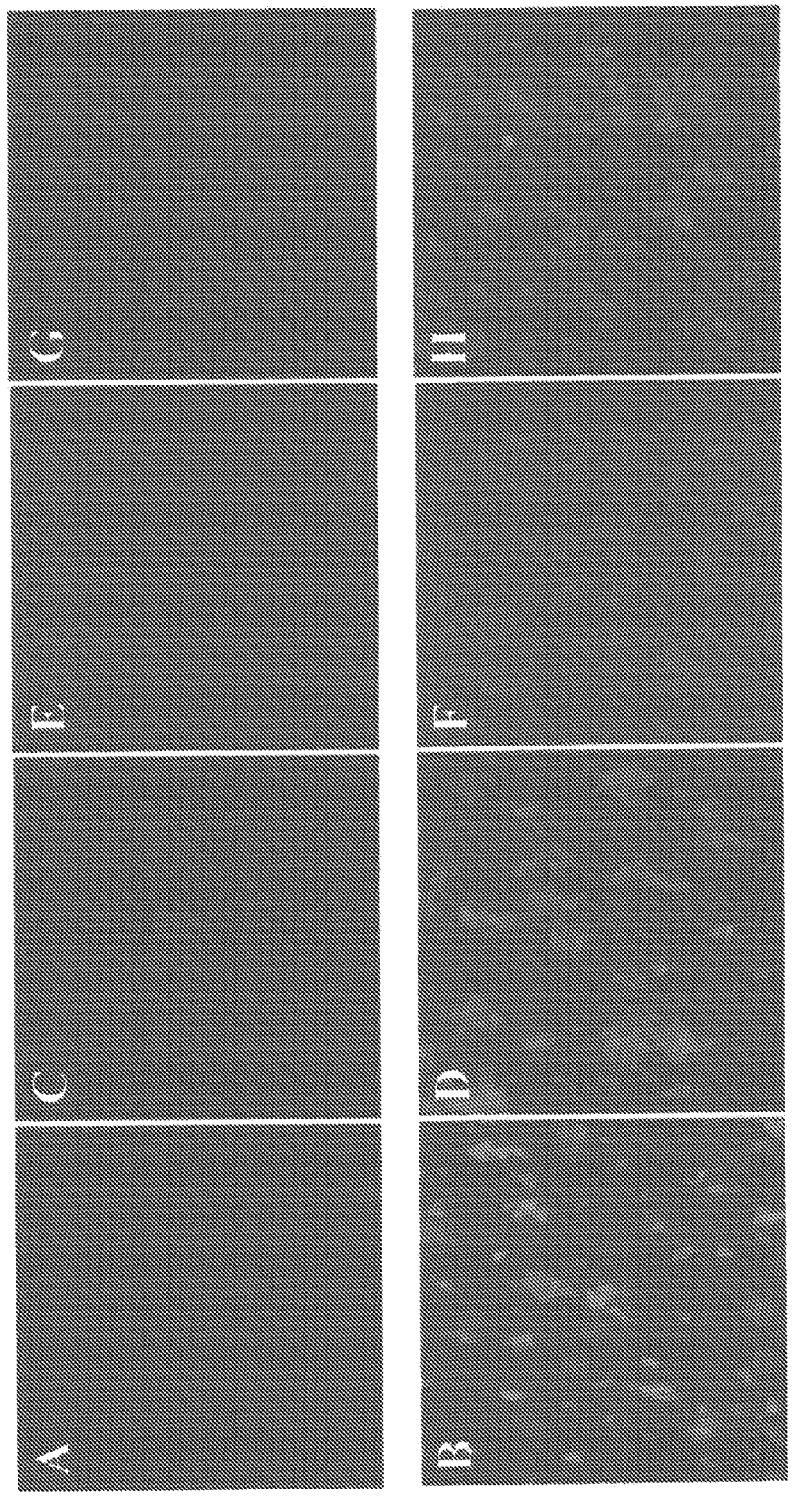
FIG. 2 provides images of liposomes which bound hydroxyapatite (HA) particles. The liposomes tested are conventional liposomes loaded with Rhodamine B, fluorescence, β-carotene, or FITC loaded HPMA copolymer (FIGS. 2A, 2C, 2E, and 2G, respectively) and biomineral-binding liposomes loaded with Rhodamine B, fluorescence, β-carotene, or FITC loaded HPMA copolymer (FIGS. 2B, 2D, 2F, and 2H, respectively).

HA particles (100 mg/tube) were mixed with the liposome solutions (1 mL) in eppendorf centrifuge tubes. The tubes were then placed on a Labquake® rotator to allow binding at room temperature for 30 minutes. The tubes were centrifuged at 7,000 rpm for 5 minutes and the supernatants were withdrawn. PBS (1 mL×6) was added, vortexed, and centrifuged to wash out unbound liposomes. The liposome bound HA particles were then lyophilized. The dried samples were then investigated under florescence microscope. The results showed that biomineral-binding liposomes loaded with hydrophilic, hydrophobic, polymeric model drugs have a strong binding ability on HA particles (FIG. 2).

Example 2

Preparation of Sodium Fluoride Loaded Liposomes and Their Binding Ability on Hydroxyapatite (HA)

The standard sonication method was used to prepare sodium fluoride loaded liposomes. Briefly, for the preparation of biomineral-binding liposomes, egg phosphatidylcholine (200 mg), cholesterol (80 mg), and ALN-TEG-Chol (40 mg) were dissolved in $CHCl_3$/methanol (4 mL). For the preparation of nonbiomineral-binding liposomes, egg phosphatidylcholine (200 mg) and cholesterol (100 mg) were dissolved in $CHCl_3$/Methanol (4 mL). The lipid solutions were transferred into flasks and dried by evaporation under a nitrogen stream. The samples were then stored under vacuum for 4 hours at 4° C. The thin lipid film formed on the wall of flask was hydrated with a sodium fluoride solution (4 mL, 0.15 M) and sonicated under nitrogen for 5 minutes (30 seconds on and 30 seconds off for each cycle) with a probe sonicator. Subsequent centrifugation with 10,000 rpm and purification with Sephadex® G-25 were carried out to remove untrapped sodium fluoride.

HA particles (150 mg/tube×5) were added into the liposome solutions in eppendorf centrifuge tubes (1 mL×5), and then placed on a Labquake® rotator to allow binding at room temperature for 1 hour. The tubes were centrifuged at 7,000 rpm for 5 minutes and the supernatants were withdrawn. Aaline (1 mL×6, 0.15M) was added, vortexed, and centrifuged to wash out unbound liposomes. THF (1 mL×2), THF/Water (1 mL×2, 1:1, v/v), water (1 mL×2) was added, vortexed, and centrifuged to extract binding lipids and sodium fluoride. The solution was combined and concentrated. Chloroform (10 mL×3) was added to extract lipids from water. The water layer containing sodium fluoride was evaporated in vacuum. The sodium fluoride bound on HA was then quantified by $^{19}F$ NMR with 0.5 µM pentafluorophenol as internal standard. The results showed that the binding efficacy of biomineral-binding liposomes containing sodium fluoride on HA is 407 µg sodium fluoride per gram of HA. The nonspecific binding of nonbiomineral-binding liposomes containing sodium fluoride on HA was only 270 µg sodium fluoride per gram of HA.

Example 3

Autoclaved HA discs (0.5' diameter×0.04-0.06' thick) were incubated with different liposome solutions, free oxacillin solution or 3% sodium chloride solution in a 24-well plate for 1 hour and then extensively washed to remove unbound liposome or drug. The HA discs were then transferred to wells containing 1 mL of S. aureus suspension (OD=0.05 at 600 nm) in Trypticase Soy Broth (TSB) and cultured statically for 24 hours to allow biofilm growth at 37° C., prior to quantification of bacterial growth. At the end of each experiment, the surface of each HA disc was gently scraped with a sterile spatula to harvest adherent cells. The removed biofilms were subjected to vortex mixing for 10 seconds and then serially diluted in TSB broth at a 1:10 ratio. The number of viable cells in each sample was quantified using the track dilution method. All plates were incubated for 24 hours at 37° C. and then the CFUs recovered per biofilm were determined. Specific differences between the log-CFU/biofilm of each experimental group were analyzed using the Student t-test. A p-value of <0.05 was considered as statistically significant.

Figure 3:
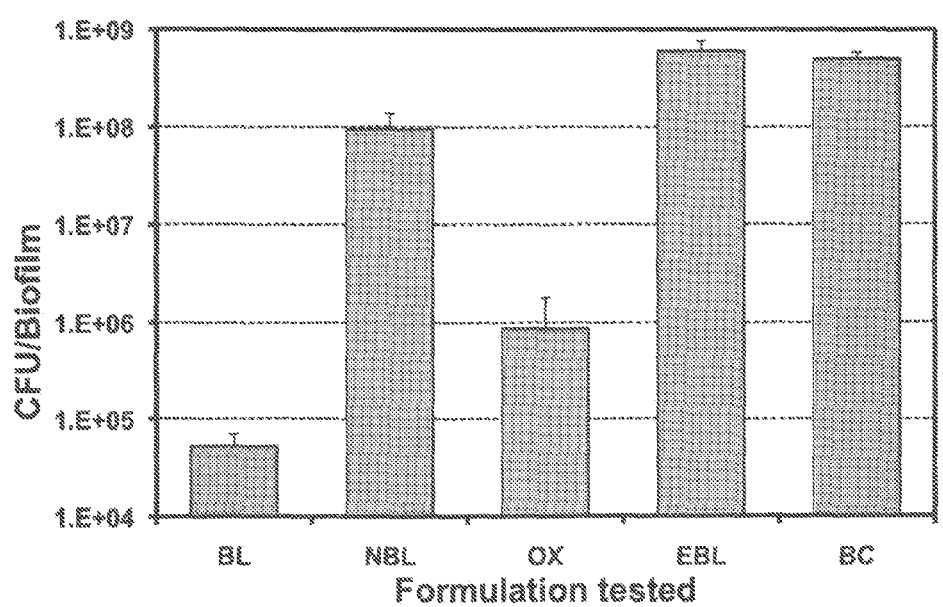
FIG. 3 is a graph of the colony forming units per biofilm of S. aureus for the indicated formulations. OX=oxacillin; BL=Binding liposome with oxacillin; NBL=non-binding liposome with oxacillin; EBL=empty binding liposome; BC=blank control.

The results demonstrate that the oxacillin containing biomineral-binding liposome (BBL) showed strong inhibition of biofilm formation on HA discs when compared to the blank control (BC) and the effect was also significantly stronger than that of oxacillin containing non-binding liposome (NBL) and that of the free drug oxacillin (OX) (FIG. 3). The oxacillin containing NBL also displayed a weaker, albeit significant, inhibitory effect when compared to BC. The vesicles itself (empty biomineral-binding liposome, EBL) did not show any inhibition on biofilm formation.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A liposome comprising at least one functionalized cholesterol of the formula: Chol-X-T, wherein X is a linker domain, T is at least one targeting moiety which binds hard tissue and/or medical implants, and Chol is cholesterol or a derivative or analog thereof, wherein said liposome encapsulates at least one therapeutic agent for the treatment of an oral disease or disorder, and wherein said functionalized cholesterol has the formula:

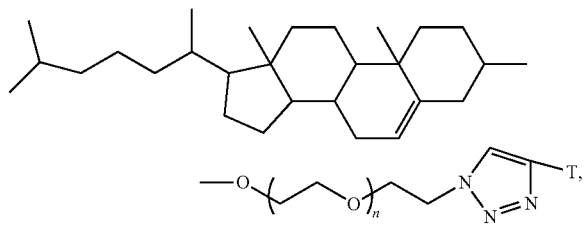

wherein n is 0 to about 10.

2. The liposome of claim 1, wherein said targeting moiety is selected from the group consisting of bisphosphonates, alendronate, tetracycline, tetracycline analogs, sialic acid, malonic acid, N,N-dicarboxymethylamine, 4-aminosalicyclic acid, 5-aminosalicyclic acid, antibodies or fragments or derivatives thereof specific for hard tissue or implant material, and peptides comprising about 2 to about 100 amino acids selected from the group consisting of D-glutamic acid, L-glutamic acid, D-aspartic acid, L-aspartic acid, D-phosphoserine, L-phosphoserine, D-phosphothreonine, L-phosphothreonine, D-phosphotyrosine, and L-phosphotyrosine.

3. The liposome of claim 2, wherein said targeting moiety is alendronate.

4. The liposome of claim 1, wherein said functionalized cholesterol has the formula:

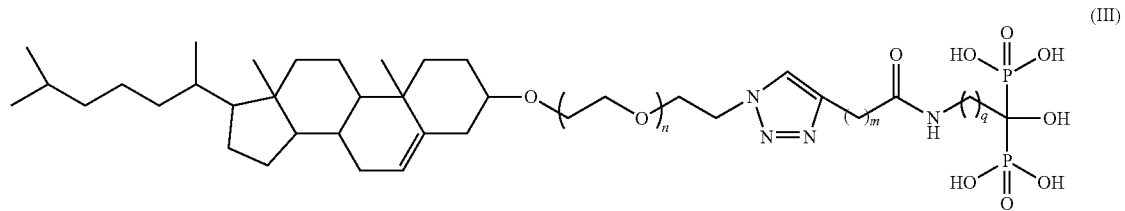
(III)

wherein n is 0 to about 10; wherein m is 1 to about 10; and q is 1 to about 10.

5. The liposome of claim 1, wherein said liposome further encapsulates at least one detectable agent.

6. The liposome of claim 1, wherein said therapeutic agent comprises fluoride.

7. A composition comprising at least one liposome of claim 1 and at least one pharmaceutically acceptable carrier.

8. A method of inhibiting a bone related disease or disorder and/or oral disease or disorder, said method comprising administering the composition of claim 7 to a subject.

9. The liposome of claim 1, wherein said therapeutic agent is selected from the group consisting of menthol, a fragrant agent, a flavoring agent, cooling agent, fluoride, vitamins, neutraceuticals, tooth whitening agents, tooth coloring agents, bleaching or oxidizing agents, thickening agents, and sweetening agents.

* * * * *